United States Patent [19]

Leute

[11] 4,025,501
[45] May 24, 1977

[54] POLYPEPTIDE PROPOXYPHENE DERIVATIVES FOR IMMUNOASSAY REAGENTS

[75] Inventor: Richard K. Leute, Mountain View, Calif.

[73] Assignee: Syva Company, Palo Alto, Calif.

[22] Filed: Mar. 20, 1975

[21] Appl. No.: 560,079

[52] U.S. Cl. .............................. 260/121; 23/230 B; 195/63; 195/68; 195/103.5 R; 260/112 R; 260/112 B; 260/78 A; 260/463; 260/570.5 R; 260/576; 424/12; 424/85; 424/88
[51] Int. Cl.² ......................................... C07G 7/00
[58] Field of Search ......... 260/112 R, 121; 195/63, 195/66, 68

[56] References Cited

UNITED STATES PATENTS

| | | | |
|---|---|---|---|
| 3,690,834 | 9/1972 | Goldstein et al. | 23/230 |
| 3,817,837 | 6/1974 | Rubenstein et al. | 195/63 |
| 3,852,157 | 12/1974 | Rubenstein et al. | 195/63 |

OTHER PUBLICATIONS

J. Am. Chem. Soc. 75, 4458–4461, (1953), Pottland et al.

*Primary Examiner*—Howard E. Schain
*Attorney, Agent, or Firm*—Townsend and Townsend

[57] ABSTRACT

Novel compounds are provided which are derivatives of 1,2-diphenyl-3-methyl-4-dimethylamino-2-butanol. The indicated alcohol is employed to prepare the monoester of a dibasic acid which is conjugated with an antigen for the production of antibodies which recognize both propoxyphene and its N-desmethyl metabolite in immunoassays.

8 Claims, No Drawings

POLYPEPTIDE PROPOXYPHENE DERIVATIVES FOR IMMUNOASSAY REAGENTS

BACKGROUND OF THE INVENTION

1. Field of the Invention

Propoxyphene finds wide use as an analgesic in that it affords pain relief while having fewer side effects than codeine. Propoxyphene finds a place in the battery of drugs employed for the medical treatment of people. Because of propoxyphene's effect on the central nervous system, the use of propoxyphene has become abused. That is, the drug has become sold on the street and is used in other than medicinal treatment. It has, therefore, become a matter of concern to detect those users of the drug, who use the drug without medical authorization.

There are a number of different ways for detecting the presence of a drug in urine. Some of these techniques employ chromatographic techniques such as vapor phase chromatography, thin-layer chromatography, and the like. These techniques depend upon the properties of adsorption of the drug of interest, which allow for the drug to be separated from other materials in the sample being tested. Another group of techniques rely on the ability of a receptor such as an antibody, to distinguish the molecule of interest from other molecules which may be present. These techniques are referred to as immunoassays since they depend on a mammalian immunological response for the production of the antibodies which recognize the compound of interest.

In producing antibodies, one normally conjugates a molecule which resembles the compound of interest to a large molecule which is antigenic. The resulting conjugate is then injected into an animal, normally a domestic animal, to elicit an immunological response with the production of antibodies which recognize the compound of interest.

In producing antibodies, there are a number of considerations as to the usefulness of the antibody composition in an immunoassay. The concentration of useful antibodies must be sufficiently high, so that upon dilution in the assay, there is sufficient antibody to provide for the necessary sensitivity. The binding constant of the antibody should also be high, so that large concentrations of antibodies are not required to ensure a reasonable amount of binding of any of the compound present to the antibody. It should be recognized that normally the concentrations of interest are only a few micrograms per milliliter or less so that one is dealing with extremely small amounts of the compound being assayed. In addition, it is desirable that the antibody have a certain degree of specificity. In some instances, only one compound is of interest. In other instances, the antibody should not only recognize the specific compound of interest, but also metabolites having similar structure, but differing in the presence or absence of a substituent.

2. Description of the Prior Art

U.S. Pat. No. 3,817,837 describes a homogeneous enzyme immunoassay technique, as well as enzyme conjugates for use in the assay. Included among potential conjugates are propoxyphene derivatives. U.S. Pat. No. 3,690,834 describes a homogeneous immunoassay employing a free radical detector. Included among potential reagents are spin labeled propoxyphenes.

SUMMARY OF THE INVENTION

Compounds are provided for conjugation to antigens for the production of antibodies which recognize propoxyphene and its metabolite, as well as conjugation to detector molecules such as stable free radicals and enzymes for use as reagents in immunoassays. The alcohol 1,2-diphenyl-3-methyl-4-dimethylamino-2-butanol is conjugated to a dibasic acid to form a half acid ester. The acid group may then be activated in a variety of ways for conjugation to amines to form amide linkages. The conjugate to antigenic proteins or polypeptides can be used for the formation of antibodies which have high specificity for propoxyphene and its desmethyl metabolite.

DESCRIPTION OF THE SPECIFIC EMBODIMENTS

Novel compounds are provided which are used in the formation of reagents for use in immunoassays. A diphenyl amino alcohol is conjugated to a dibasic acid to provide a half acid ester which may then be employed for conjugation to a polypeptide or protein through an amide link to provide antigens. Alternatively, the dibasic acid may be conjugated to amino substituted stable free radicals or through amino groups and amide linkages to enzymes to prepare detector reagents for use in immunoassays.

The conjugated antigen is injected according to conventional ways into vertebrates, particularly mammals, and more particularly domestic animals, e.g. bovine, ovine, hares, etc., to provide high titers of antibodies which are highly specific for the compounds of interest.

For the most part, the compounds or compositions of interest of this invention will have the following formula:

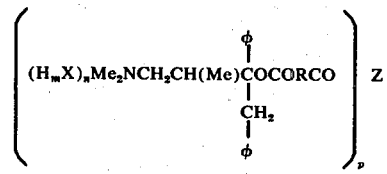

wherein:
R is a bond or a divalent aliphatic radical having from 0 to 1 site of ethylenic unsaturation and of from 1 to 5, more usually 2 to 4, and preferably 2 carbon atoms;
X is an anion of a strong mineral acid, normally sulfate, halide, or the like, $m$ is equal to the valence of X and $n$ is 0 to 1 divided by $m$;
Z is hydroxyl, alkoxyl of from 1 to 6 carbon atoms, more usually of from 1 to 3 carbon atoms, alkyl carbonate ($OCO_2R^1$, wherein $R^1$ is alkyl of from 1 to 6 carbon atoms, more usually 1 to 4 carbon atoms), Y, wherein Y is a polypeptide residue (including polypeptide subunits of proteins); and
$p$ is 1 except when Z is Y, when p will be equal to the number of acyl groups bonded to the amino groups of Z, and will be at least 1, and not greater than the number of the amino functional groups available for bonding, usually not more than the molecular weight of Z divided by 500, more usually not more than the molecular weight divided by 1500, and usually at least 1 per 50,000 molecular weight.

The carboxylic acid and ester OW (Z = OW) will for the most part have the following formula:

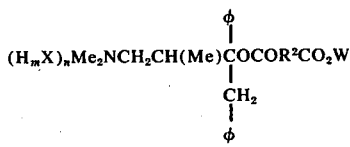

wherein:

X, $m$ and $n$ have been defined previously;

$R^2$ is a bond or aliphatic divalent radical having from 0 to 1 site of ethylenic unsaturation, and of from 1 to 5 carbon atoms, preferably of from 2 to 4 carbon atoms, and more preferred of 2 carbon atoms and saturated, i.e. ethylene; and W is hydrogen or alkyl of from 1 to 6, usually 1 to 4 carbon atoms.

Illustrative groups for R (including $R^2$) are methylene, ethylene, 1,2-propylene, butylene, ethenylene, etc.

Of particular interest are compounds where the carboxyl group is bonded to an amino group, which is part of a polypeptide or protein structure. One group of polypeptides and proteins is antigenic, so that by bonding the carboxyl modified subject aminoalcohol to the polypeptide or protein, antibodies can be formed to the aminoalcohol. A narrower class of proteins, which also can be used as antigens, but will not normally be used as such, are enzymes which are employed as the detector in an immunoassay system. As antigens, inactive enzymes can be used.

Polypeptides usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 amino acid groups (or 10,000 to 35,000 molecular weight). For the purpose of this invention, polypeptide is intended to include individual polypeptide units and polypeptides which are subunits of proteins, whether composed solely of polypeptide units or polypeptide units in combination with other functional groups, such as porphyrins, as in haemoglobin or cytochrome oxidase.

The number of propoxyphene groups will vary depending on whether the polypeptide is an enzyme or antigen. The maximum number of groups will be limited by the effect of substitution on solubility, activity, and the like. For the formation of antibodies, a sufficient number of propoxyphene groups should be present, so as to provide a satisfactory harvest of antibodies to propoxyphene. Otherwise, the proportion of antibodies to propoxyphene as compared to other compounds may be undesirably low.

The first group of protein materials or polypeptides which will be considered are the antigenic polypeptides. These may be joined to the non-oxo-carbonyl group of the propoxyphene analog through an amino group. The amide product can be used for the formation of antibodies to propoxyphene. The protein materials which may be used will vary widely, and will normally be from 1,000 to 10 million molecular weight, more usually 20,000 to 500,000 molecular weight.

With the antigens, there will be no more than one propoxyphene group per 500, more usually 1,000 molecular weight, generally no more than one propoxyphene group per 2,000 molecular weight, and not less than one propoxyphene group per 100,000 molecular weight, usually not less than one propoxyphene group per 50,000 molecular weight. With intermediate molecular weight antigens, those having molecular weights in the range of 20,000 to 1,000,000 the number of propoxyphene groups will generally be from about 2 to 250, usually from 4 to 100. Low molecular weight antigens (1,000 to 5,000 molecular weight) may have 1 to 10, usually 2 to 5 propoxyphene groups, so that there may frequently be as many as one propoxyphene group per 500 molecular weight.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended, when speaking of enzyme molecular weights, to refer to the entire enzyme. There will be on the average at least about one propoxyphene per enzyme, usually at least about two propoxyphenes per enzyme when the labeling is not limited to a specific amino group, and rarely more than 40 propoxyphenes per enzyme, usually not more than 30 propoxyphenes per enzymes. For example, with lysozyme the average number of propoxyphene groups will be in the range of about 2 to 4.

While the propoxyphene analog may be bonded through the carboxyl group to hydroxyl or mercapto groups, which are present in the proteins, for the most part the bonding will be to amino. Therefore, the compounds are described as amides, although esters and thioesters may also be present.

Amino acids present in proteins which have free amino groups for bonding to the carboxy modified propoxyphene include lysine, arginine, ornithine, etc. The hydroxyl and mercaptan containing amino acids include serine, cysteine, and threonine.

Various protein and polypeptide types may be employed as the antigenic material. These types include albumins, enzymes, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tyrosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the carboxy modified propoxyphenes may be conjugated. As indicated, the propoxyphene modified enzyme is useful for immunoassays. A description of the immunoassay technique will follow.

Various enzymes may be used such as peptidases, esterases, amidases, phosphorylases, carbohydrases, oxidases, reductases, and the like. Of particular interest are such enzymes as lysozyme, peroxidase, α-amylase, dehydrogenases, particularly malate dehydrogenase and glucose-6-phosphate dehydrogenase, alkaline phosphatase, β-glucuronidase, cellulase and phospholipase. In accordance with the I.U.B. Classification, the enzymes of interest are: 1. Oxidoreductases, particularly Groups 1.1, and more particularly 1.1.1, and 1.11, more particularly, 1.11.1; and 3. Hydrolases, particularly 3.2, and more particularly 3.2.1.

The substituted proteins will for the most part have the following formula:

$$(M-R^2-CO-)_{n'}Y'$$

wherein

Y' is a polypeptide residue usually antigenic;
$R^2$ has been defined previously; and
M is the residue bonded to $R^2$ of the formula:

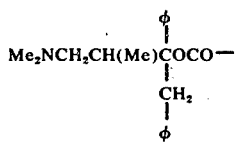

$n'$ will usually be of from 1 to 50, more usually from 2 to 35, when Y' is an enzyme residue. When Y' is an antigenic protein residue, $n'$ will usually range from the molecular weight of the protein divided by about 1,000, usually 1,500 to about 50,000. For small polypeptides, $n'$ will usually range from 1 to the molecular weight of the polypeptide divided by 500. For antigenic proteins of from 20,000 molecular weight to 1,000,000 molecular weight, $n'$ will generally average from 2 to 250.

Instead of an enzyme a stable free radical may be employed as the functionality for detection in the immunoassay. The stable free radicals are cyclic nitroxides having the nitrogen of the nitroxide as an annular member and from 0 to 1 other heteroatoms, i.e. oxygen and nitrogen, as annular members. The stable free radical molecules bonded to the non-oxo-carbonyl of the propoxyphene derivatives will normally be from 7 to 16 carbon atoms, more usually from 7 to 12 carbon atoms. The amino functionality may be bonded directly to the annular carbon atom or may be bonded to the ring through an aliphatic chain of from 1 to 4 carbon atoms, more usually of from 1 to 2 carbon atoms. The molecules may have from 0 to 2 sites of ethylenic unsaturation, more usually from 0 to 1 site of ethylenic unsaturation.

For the most part, the stable nitroxide functionalities bonded to the carboxyl carbonyl of the carboxyl modified propoxyphene will have the following formula:

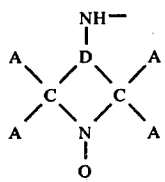

wherein:
D is a divalent aliphatic radical usually aliphatically saturated of from 1 to 6 carbon atoms, more usually of from 1 to 3 carbon atoms, only from 1 to 3, usually 2 to 3 of the carbon atoms in D being annular atoms; and
A is lower alkyl (1 to 6, usually 1 to 3 carbon atoms), particularly methyl.

For the most part, compounds are pyrrolidine or piperdine derivatives, and D is hydrocarbon.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile and hexamethylphosphoramide. The reaction is carried out by bringing the various reagents together under mild conditions and allowing sufficient time for the reaction to occur.

A second method is to form a mixed anhydride employing an alkyl chloroformate, e.g. isobutyl chloroformate. The mixed anhydride is formed by combining the carboxy substituted propoxyphene, the alkyl chloroformate and a tertiary amine. The temperature is normally below ambient temperature. The mixture is then combined with the amino compound to be conjugated and the reaction allowed to proceed under mild conditions.

At least a stoichiometric amount of the chloroformate is employed based on the propoxyphene derivative, and usually an excess. The excess does not usually exceed three times stoichiometric. The tertiary amine is present in at least equimolar amounts to the chloroformate.

Also, esters of the carboxy modified propoxyphene can be employed which are operative in water for acylating amine functions. An illustrative hydroxylic group is p-nitrophenol which can be used to prepare the p-nitrophenyl ester.

EXPERIMENTAL (The following examples are offered by way of illustration and not by way of limitation. All temperatures not indicated are in Centigrade.)

EXAMPLE I Methyl Succinate Monochloride

Methyl succinate (20.5 g) was heated with 20ml thionyl chloride to 40° for 3.5 hours. Excess thionyl chloride was removed by vacuum distillation (13mm Hg). The acid chloride (20.6g) was distilled at 43°–44° /0.2mm Hg.

EXAMPLE II Preparation of 4-dimethylamino-1,2-diphenyl-3-methyl-2-butyl-methyl-succinate and the hydrochloride VI 2,2-Diphenyl-3-methyl-4-(dimethylamino)butanol-2 hydrochloride (10g) was dissolved in water (~200ml) and extracted with chloroform (2 × 30ml yellow organic phase) to remove some insoluble compound. Addition of 2M potassium hydroxide to the aqueous phase gave a precipitate which was extracted with 2 × 10ml chloroform. The combined organic layers were dried over anhydrous magnesium sulfate. After filtration and evaporation of the solvent in vacuo (1 hour, 0.05mm Hg) an oil remained. It was dissolved in 150ml anhydrous toluene and heated to 100° together with 20g methyl succinate monochloride for two hours with exclusion of moisture. A precipitate formed immediately upon mixing which did not increase during the reaction. After standing overnight the precipitate was removed by filtration and centrifugation (1.2g) and the solvent was evaporated. The residue was dissolved in water and extracted with 2 × 100ml chloroform/2M potassium hydroxide. The combined organic layers gave a brown oil upon evaporation of the solvent. The oil was dissolved in anhydrous ether and hydrogen chloride passed through the solutuion. At first a precipitate occurred which later turned into an oil. The ether was decanted and the oily residue dissolved in 70ml warm benzene. Standing for two hours, gave colorless crystals which increased on scratching the flask. The crystals (8.5g) were collected and dried in vacuo (m.p. 82°–88°, gas evolution). Upon slow evaporation of the ether more colorless crystals were obtained.

For analysis the compound was recrystallized by dissolving in hot benzene and adding carbon tetrachloride.

EXAMPLE III Hydrolysis of 4-dimethylamino-1,2-diphenyl-3-methyl-2-butyl-methyl-succinate The ester of Example II (8.5g) was dissolved in 20ml water and 6g of potassium carbonate in 30ml water added. A white precipitate appeared which was extracted with chloroform (2 × 50ml). The combined organic layers were dried over anhydrous magnesium sulfate, filtered and evaporated. The purity of the ester was evidenced by a single spot in the thin layer chromatogram (ether). The solvent was evaporated and the residue dried in vacuo yielding 7g of an oil. The oil was dissolved in a solution of 100ml methanol and 30ml water containing 6g of potassium carbonate. The mixture was refluxed for 30 minutes, cooled to room temperature and evaporated. A yellowish residue remained which was dissolved in water (50ml) and extracted with 5ml ether. The aqeuous phase was diluted to 200ml and neutralized with BioRad 50W-X8 to pH 6.6. The resin had been previously washed until the washings were clear. Evaporation of the aqueous solution gave a residue which after drying in vacuo was dissolved in ethyl acetate and the insoluble part removed by centrifugation. From the ethyl acetate 5.9g of a very hygroscopic material was obtained.

EXAMPLE IV Preparation of the BSA-conjugate of 4-dimethylamino-1,2-diphenyl-3-methyl-butyl-2-succinate with Bovine Serum Albumin (BSA)

The acid of Example III (5.4g) was dissolved in 15ml DMF and 1.65 ml isobutyl chloroformate were added after the solution had been cooled to −10°. During the addition of the isobutyl chloroformate, there was a color change from slightly yellow to a slight brown. The solution was kept at −10° for 30 minutes and at 0° for 20 minutes. It was then added to a solution of 8g BSA and 23g sodium bicarbonate in 250ml water. A precipitate formed immediately when the DMF solution was added. After stirring at 0° for 6 hours, the solution was dialyzed overnight in a rocking dialyzer against distilled water with mixing inside the dialysis bag by means of a glass ball. The precipitate was removed by centrifugation at 20,000 r.p.m. (Sorvall, SS-34 rotor). The solution remained slightly opalescent. It was lyophilized and 9.2g of a white residue was obtained. For further separation 2g of the compound were dissolved in 60ml water and chromatographed on 200ml Sephadex G-25.

The hapten number was obtained by measuring the absorption at 257nm. Since propoxyphene does not absorb substantially at 280nm, the BSA concentration can be determined from this peak. The BSA absorption at 257 is one-half of the absorption at 280nm. Therefore, the absorption due to the propoxyphene hapten can be obtained by subtracting the protein absorption at 257nm from the total absorption at 257nm. The propoxyphene absorption can then be converted into propoxyphene concentration. The hapten number was between about 60 to 70.

EXAMPLE V Preparation of the propoxyphene spin label

4-Dimethylamino-1,2-diphenyl-3-methyl-2-butylsuccinate (525mg, 1.37 mmoles) were dissolved in 4ml ethyl acetate together with 207mg 3-amino-2,2,5,5-tetramethylpyrrolidinyl-1-oxyl. Dicyclohexylcarbodimid (283mg, 1.37 mmoles) was added at 0° in 2ml ethyl acetate. The reaction mixture was stirred at room temperature for 60 hours. A precipitate (30mg) formed during the first hours.

The reaction was centrifuged and the supernatant washed with water, dried over anhydrous magnesium sulfate and evaporated. The yellow residue was sublimed at 50° for 16 hours. The sublimate was the starting radical (45mg). The residue was separated by TLC on silica gel in chloroform/methanol 9:1. The band moving with an $r_f \sim 0.5$ was the desired spin label.

EXAMPLE VI Preparation of propoxyphene lysozyme conjugate

A. Into a reaction vessel was introduced 0.038g of the monoacid ester prepared above, 14μl of triethylamine, 14μl of isobutylchloroformate and 1ml of DMF. The mixture turned slightly cloudy and the reaction was allowed to continue until the mixture had turned yellow. The mixed anhydride thus prepared was then added dropwise to 120mg of lysozyme and 10ml water at pH 9.1. The mole ratio of the monoacid ester mixed anhydride to lysines of lysozyme was 2:1. A heavy white precipitate formed, with the pH rising rapidly and addition of 0.05N HCl was used to maintain the pH between 9–10. The reaction was continued for 4.5 hours and the pH was maintained by the addition of 0.05N sodium hydroxide in the range of 9.0–9.2. At the end of the reaction, the pH was adjusted to 7.0 with the precipitate dissolving and the solution dialyzed against 0.025M, pH 6.0 Tris-maleate buffer.

B. Into a reaction vessel was introduced 0.038g of the monoacid ester prepared previously, 14μl of isobutylchloroformate and 1ml of DMF. After sufficient time for completion of the formation of the mixed anhydride, the solution was then added dropwise to 120mg of lysozyme and 10ml of water at pH 9.1. The pH dropped and 0.05N sodium hydroxide was added to maintain the pH in the range of 9–10. The reaction was run for 2 hours at 4° at a pH of 9–9.5, and then adjusted to pH 8.5 with formation of a heavy white precipitate. The precipitate was removed by centrifugation, dissolved in 8M urea, and both the supernatant and the 8M urea solution dialyzed against 0.025M, pH 6.0, Tris-maleate buffer. The conjugated lysozyme in the two fractions was isolated.

Antibodies were prepared employing the conjugate of Example IV in accordance with known procedures. Goats were initially immunized with the antigen (30mg) and complete Freund's adjuvant (injected into 4 sites), followed by a schedule of further injections about 1 month apart of the antigen (30mg) with incomplete Freund's adjuvant, with the animal being bled 1 week after each injection. The sixth bleed was harvested and employed. Binding constant, $5 \times 10^6$; contration based on binding sites determined using the compound of Example V, $4 \times 10^{-5}$.

The following is the procedure for carrying out the assay.

In carrying out the assay, a number of reagent solutions are prepared:

A. Buffer solution: Tris-maleate, 0.825M, pH 6.0;

B. Bovine serum albumin solution: 0.1 weight percent BSA in Tris-maleate prepared above;

C. Bacteria: 40mg of M. luteus suspended in 50ml buffer solution. The suspension is prepared daily, 12 hours before use and stored at 4° C;

D. Propoxyphene-lysozyme: the stock solution of propoxyphene conjugated with lysozyme is diluted with 0.1 weight percent BSA and Tris-maleate and stored.

The active lysozyme content of the working solution is determined by measuring at 436nm the rate of bacteriolysis at 30°. The assay solution is prepared by mixing 0.2ml bacteria, 0.02ml, 0.1 weight percent, BSA-buffer, 0.08ml synthetic urine (or urine where appropriate) and 0.50ml of the lysozyme solution. The antibody is employed in 0.025M Tris-maleate (pH 7.4) at a concentration suitable for 20μl to inhibit 92–96 percent of the propoxylene-lysozyme activity of the stock enzyme solution. The stock enzyme solution should provide about 150 OD units from a sample having no propoxyphene to a sample where the propoxyphene saturates the available antibody binding sites. (OD units are optical density units on a U.V. spectrometer at the measurement temperature.)

To prepare synthetic urine, 5.2g potassium chloride, 8.2g sodium chloride, 1.4g sodium dihydrogenphosphate, 1.4g disodium monohydrogenphosphate, and 11g of urea are combined in 1 liter of distilled water.

In carrying out the assay, 20μl of the antibody solution is added to 0.2ml of the bacterial suspension. To this solution is added 80μl of urine and the mixture diluted with one-half ml of the enzyme solution. The mixture is then aspirated into the spectrometer and the decrease in optical density is measured at 435nm for 40 seconds. The concentration of propoxyphene in the urine sample is read from a standard curve prepared by using standardized solutions and taking readings.

Ten samples were spiked with 5.0mg/ml propoxyphene in synthetic urine and the results determined. The average value was 5.07, with a standard deviation of 0.673.

Next, a number of drugs having similar structures to propoxyphene were tested as to cross-reactivity. The results are reported as the number of micrograms required to give a reading equivalent to the presence of one microgram of propoxyphene.

TABLE I

| Drug | Equivalence to 1.0μg/ml Propoxyphene |
|---|---|
| Methadone | 370 |
| Demerol | >1000 |
| Thorazine | 140 |
| Phenergan | 200 |
| Librium | >1000 |
| Dextromethorphan | 550 |
| Codeine | >100 |

In addition, 50 urine samples were received from an independent laboratory and tested for propoxyphene. Lack of correlation with the results obtained by the independent laboratory and the results obtained by the above assay occured in only three samples. Negative results were readings which were less than 1.0μg/ml. No efforts were made to determine the basis for the discrepance. It should be noted that a major proportion of the propoxyphene is metabolized to the N-desmethyl compound, so that the subject antibody while having extremely small cross-reactivity to compounds of similar structure, e.g. methadone, is able to analyze both for the propoxyphene and its metabolite.

The subject compounds of this invention provide novel precursors to antigens, antigens and antibodies derived from antigens which find use in immunoassays. The antibodies which result have high specificity, good titers, and can be used for very sensitive assays for propoxyphene. Furthermore, the antibodies are capable of recognizing both propoxyphene and its metabolite, while distinguishing these compounds from similar compounds as methadone and dextromethorphan.

Although the foregoing invention has been described in some detail by way of illustration and example for purposes of clarity of understanding, it will be obvious that certain changes and modifications may be practiced within the scope of the appended claims.

What is claimed is:

1. Compounds of the formula:

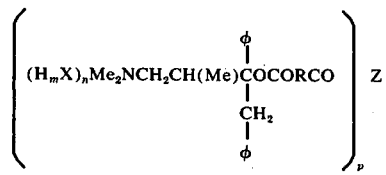

wherein:
R is a bond or divalent aliphatic radical having from 0 to 1 site of ethylenic unsaturation and of from 1 to 5 carbon atoms;
X is an anion of a strong mineral acid;
m is equal to the valence of X;
n is 0 to 1 divided by m;
Z is a polypeptide residue; and
p is equal to at least 1 and not greater than the molecular weight of Z divided by 500;
wherein the bonds to Z are through an amide link.

2. A compound of the formula:

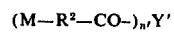

wherein:
Y' is an antigenic polypeptide residue;
R² is an aliphatic divalent radical having from 0 to 1 site of ethylenic unsaturation and of from 1 to 5 carbon atoms;
M is the residue bonded to R² of the formula:

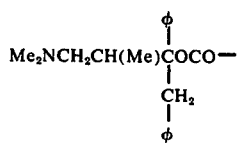

n' ranges on the average from the molecular weight of the protein divided by about 500 to the molecular weight of the protein divided by about 50,000.

3. A compound according to claim 2, wherein n' is on the average from 2 to 250 and R² is of from 2 to 4 carbon atoms.

4. A composition according to claim 3, wherein R² is of 2 carbon atoms.

5. Antibodies prepared in response to an antigen according to claim 2, capable of binding to said antigen and propoxyphene.

6. Antibodies prepared in response to said composition of claim 6, and capable of binding to said composition and propoxyphene.

7. Antibodies prepared in response to said composition of claim 4, and capable of binding to said composition and propoxyphene.

8. A compound of the formula

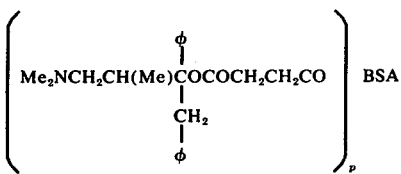

wherein:
p is at least 1 and not greater than the molecular weight of BSA divided by 1500, and BSA is bovine serum albumin.

* * * * *